United States Patent
Taube

(10) Patent No.: US 11,612,706 B2
(45) Date of Patent: Mar. 28, 2023

(54) METHODS, SYSTEMS, AND DEVICES FOR CONTROLLING MECHANICAL VENTILATION

(71) Applicant: John C. Taube, Raleigh, NC (US)

(72) Inventor: John C. Taube, Raleigh, NC (US)

( * ) Notice: Subject to any disclaimer, the term of this patent is extended or adjusted under 35 U.S.C. 154(b) by 793 days.

(21) Appl. No.: 16/693,936

(22) Filed: Nov. 25, 2019

(65) Prior Publication Data

US 2022/0409837 A1 Dec. 29, 2022

(51) Int. Cl.
*A61M 16/00* (2006.01)
*A61M 16/10* (2006.01)
(Continued)

(52) U.S. Cl.
CPC ....... *A61M 16/024* (2017.08); *A61B 5/14551* (2013.01); *A61M 16/1005* (2014.02);
(Continued)

(58) Field of Classification Search
CPC .............. A61M 16/022; A61M 16/024; A61M 16/1005; A61M 2016/102;
(Continued)

(56) References Cited

U.S. PATENT DOCUMENTS 2,414,747 A 1/1947 Kirschbaum
3,734,091 A 5/1973 Taplin
(Continued)

FOREIGN PATENT DOCUMENTS

CA 2545570 A1 9/2005
CA 2691377 A1 1/2009
(Continued)

OTHER PUBLICATIONS

Sano, A.; Kikucki, M.; Adaptive control of arterial oxygen pressure of newborn infants under incubator oxygen treatments, IEE Proceedings D (Control Theory and Applications), 1985, 132, (5), p. 205-211 (Year: 1985).*

(Continued)

*Primary Examiner* — Joseph D. Boecker
*Assistant Examiner* — Thomas W Greig
(74) *Attorney, Agent, or Firm* — NK Patent Law

(57) ABSTRACT

Disclosed herein are methods, systems, and devices for controlling a gas mixture within a mechanical ventilator. According to one embodiment, a computer implemented method includes receiving first peripheral arterial oxygen saturation ($SpO_2$) data from a pulse oximeter via a pulse oximeter interface, wherein the pulse oximeter is configured to monitor a patient receiving invasive ventilation; determining a first mode of operation for a ventilator mechanism, wherein the ventilator mechanism is configured to provide at least a portion of the invasive ventilation; determining first partial pressure of oxygen ($PaO_2$) data stored in a first lookup table using the first $SpO_2$ data, wherein the first lookup table is derived from a sigmoid shaped oxyhemoglobin dissociation curve; determining first fraction of inspired oxygen in air ($FiO_2$) data for setting a mixture in a gas blender in the ventilator mechanism based on the first $PaO_2$ data and a variable offset; and providing the $FiO_2$ data to the ventilator mechanism.

17 Claims, 4 Drawing Sheets

(51) Int. Cl.
*A61B 5/1455* (2006.01)
*A61M 16/12* (2006.01)

(52) U.S. Cl.
CPC ..... *A61M 16/12* (2013.01); *A61M 2016/1025* (2013.01); *A61M 2205/3306* (2013.01); *A61M 2205/502* (2013.01); *A61M 2205/52* (2013.01); *A61M 2230/20* (2013.01)

(58) Field of Classification Search
CPC .......... A61M 2016/1025; A61M 16/10; A61M 16/12–127
See application file for complete search history.

(56) References Cited

U.S. PATENT DOCUMENTS

| | | | |
|---|---|---|---|
| 4,325,413 | A | 4/1982 | Lenhart et al. |
| 4,584,996 | A | 4/1986 | Blum |
| 4,665,911 | A | 5/1987 | Williams et al. |
| 4,765,340 | A | 8/1988 | Sakai et al. |
| 4,889,116 | A * | 12/1989 | Taube ............... A61M 16/00 128/204.23 |
| 5,003,985 | A | 4/1991 | White et al. |
| 5,103,814 | A | 4/1992 | Maher |
| 5,178,151 | A | 1/1993 | Sackner |
| 5,388,575 | A | 2/1995 | Taube |
| 6,148,814 | A * | 11/2000 | Clemmer ............ A61M 16/024 600/529 |
| 6,186,142 | B1 | 2/2001 | Schmidt et al. |
| 6,561,187 | B2 | 5/2003 | Schmidt et al. |
| 7,329,038 | B2 | 2/2008 | Hashiba |
| 7,802,571 | B2 | 9/2010 | Tehrani |
| 8,194,944 | B2 | 6/2012 | Tivig et al. |
| 8,434,481 | B2 | 5/2013 | Ogilvie et al. |
| 8,434,483 | B2 | 5/2013 | Patel et al. |
| 8,434,484 | B2 | 5/2013 | Patel |
| 8,434,523 | B2 | 5/2013 | Suharno |
| 8,801,619 | B2 | 8/2014 | Baker, Jr. et al. |
| 10,007,238 | B1 * | 6/2018 | Taube ............... G05B 13/0205 |
| 10,514,662 | B1 | 12/2019 | Taube |
| 2001/0035185 | A1 | 11/2001 | Christopher |
| 2002/0017302 | A1 | 2/2002 | Fukunaga et al. |
| 2002/0112726 | A1 * | 8/2002 | Schmidt ............ A61M 16/0677 128/204.23 |
| 2003/0013980 | A1 | 1/2003 | Starr et al. |
| 2003/0111078 | A1 * | 6/2003 | Habashi ............. A61M 16/024 128/204.18 |
| 2003/0211244 | A1 | 11/2003 | Li et al. |
| 2003/0216285 | A1 | 11/2003 | Dumont et al. |
| 2004/0054261 | A1 | 3/2004 | Kamataki et al. |
| 2004/0230108 | A1 | 11/2004 | Melker et al. |
| 2005/0051168 | A1 | 3/2005 | DeVries et al. |
| 2005/0109340 | A1 | 5/2005 | Tehrani |
| 2005/0222503 | A1 | 10/2005 | Dunlop et al. |
| 2005/0247311 | A1 | 11/2005 | Vacchiano et al. |
| 2007/0137107 | A1 | 6/2007 | Barnicki |
| 2008/0156328 | A1 | 7/2008 | Taube |
| 2008/0183057 | A1 | 7/2008 | Taube |
| 2009/0090363 | A1 | 4/2009 | Niland et al. |
| 2009/0305214 | A1 | 12/2009 | Pybus et al. |
| 2010/0175695 | A1 | 7/2010 | Jamison |
| 2010/0224191 | A1 | 9/2010 | Dixon et al. |
| 2011/0152648 | A1 | 6/2011 | Rustick |
| 2011/0190611 | A1 | 8/2011 | Rabi |
| 2011/0200392 | A1 | 8/2011 | Moncrief, III |
| 2011/0319783 | A1 | 12/2011 | Lindholt et al. |
| 2012/0016219 | A1 | 1/2012 | Fujii |
| 2012/0090611 | A1 | 4/2012 | Graboi et al. |
| 2012/0325207 | A1 | 12/2012 | Fromage |
| 2013/0030267 | A1 | 1/2013 | Lisogurski et al. |
| 2013/0174841 | A1 | 7/2013 | McAuley et al. |
| 2013/0263855 | A1 | 10/2013 | Tivig et al. |
| 2013/0276780 | A1 | 10/2013 | Tobia et al. |
| 2014/0166005 | A1 | 6/2014 | Tatkov et al. |
| 2015/0059754 | A1 | 3/2015 | Chbat et al. |
| 2015/0107588 | A1 | 4/2015 | Cheung et al. |
| 2015/0320953 | A1 | 11/2015 | Acker et al. |
| 2016/0121063 | A1 | 5/2016 | Tatkov et al. |
| 2016/0361508 | A1 | 12/2016 | Cohen |
| 2017/0143538 | A1 | 5/2017 | Lee et al. |
| 2020/0170513 | A1 | 6/2020 | Walker |

FOREIGN PATENT DOCUMENTS

| | | |
|---|---|---|
| CA | 2827253 A1 | 9/2012 |
| WO | 9624402 | 8/1996 |
| WO | WO2002056931 A2 | 7/2002 |
| WO | WO2005038690 A2 | 4/2005 |
| WO | WO2005051280 A2 | 6/2005 |

OTHER PUBLICATIONS

PCT, International Search Report and Written Opinion in International application No. PCT/US2020/062118 dated Mar. 11, 2021.
WIPO, International Preliminary Report on Patentability for PCT Patent Application No. PCT/US2020/057823, dated May 10, 2022, 9 pages.
WIPO, International Preliminary Report on Patentability for PCT Patent Application No. PCT/US2020/062118, dated May 17, 2022, 6 pages.
Branson, et al., "Is Humidification Always Necessary During Non-invasive Ventilation in the Hospital?", Respiratory Care, vol. 55, No. 2, Feb. 2010.
Anon., "Critical Care Therapy and Respiratory Care Section", National Institutes of Health, 1112000.
Sano, et al., Adaptive control of arterial oxygen pressure of newborn infants under incubator oxygen treatments, IEE Proceeding, vol. 132, Pt. D., No. 5, Sep. 1985.
Anon., "Analog Dialogue: Pulse Oximeter", Analog Devices, Inc., 1995-2014.
Soto, et al., "Automatic Ventilation Control", Freescale.com/beyondbits, undated, downloaded Sep. 17, 2014.
Elleau, et al., "Helium-Oxygen mixture in respiratory distress syndrome: a double blind study", J Pediatr., 122 (1):132-6, Abstract, Jan. 1993.
Davies, et al., "Inspired Gas Temperature in Ventilated Neonates", Pediatric Pulmonology 38:50-54, 2004.
Carter, et al., "Evaluation of heliox in children hospitalized with acute sever asthma. A randomized crossover trial", Abstract, Chest, 109(5):1256-61, May 1996.
Adawy, et al., "Design of Fuzzy Controller for Supplying Oxygen in Sub-acute Respiratory Illnesses", IJCSI, vol. 9, Issue 3, No. 1, May 2012.
Kass, et al., "Heliox therapy in acute severe asthma", Abstract, Chest, 107(3):757-60, Mar. 1995.
Kudukis, et al., "Inhaled helium-oxygen revisited: effect of inhaled helium-oxygen during the treatment of status asthmaticus in children", Abstract, J Pediatr., 130(2):217-24, Feb. 1997.
Lu, et al., "Helium-Oxygen in Treatment of Upper Airway Obstruction", Anestheology, vol. 45, Dec. 1976.
Manthous, et al., "Heliox improves pulsus paradoxus and peak expiratory flow in nonintubated patients with severe asthma", Am J Respir Crit Care Med. Abstract, 151(2pt 1):310-4, Feb. 1995.
Martin-Barbaz, et al., "Use of helium oxygen mixtures in status asthmaticus", Abstract, Rev Pneumol Clin. 43 (4): 186-9, 1987.
Anon.,"MR850 Respiratory Humidifier", Fisher & Paykel, REF 185042343, Rev. J, Aug. 2012.
Anon., "Oxygen Saturation", date unknown, downloaded Aug. 20, 2014.
Alkurawy, "Design of an Efficient Controller for Arterial Oxygen Saturation in Neonatal Infants", PhD Thesis, University of Missouri-Columbia, Dec. 2013.
Sauder, et al., "Helium-oxygen and conventional mechanical ventilation in the treatment of large airway obstruction and respiratory failure in an infant", Abstract, South Med J. 84(5):646-8, May 1991.
Shiue, et al., "The use of helium-oxygen mixtures in the support of patients with status asthmaticus and respiratory acidosis", J Asthma, Abstract, 26(3):177-80, 1989.

(56) References Cited

OTHER PUBLICATIONS

Swidwa, et al., "Helium-oxygen breathing in severe chronic obstructive pulmonary disease", Abstract, Chest, 9=87 (6):790-5, Jun. 1985.
Panchal, et al., "Feedback-Controlled System to Titrate Oxygen Delivery", Drexel University, Winter 2014.
Ardizzoni, "The incredible versatile op amp in medical apps", Analog devices, Nov. 2, 2009.
Wolfson, et al., "Mechanics and energetics of breathing helium in infants with bronchopulmonary dysplasia", Abstract, J Pediatr., 104(5):752-7, May 1984.
USPTO, Non-Final Rejection in U.S. Appl. No. 16/003,508 dated Jun. 27, 2019.
USPTO, Non-Final Rejection in U.S. Appl. No. 14/602,392 dated Oct. 3, 2017.
USPTO, Final Office Action in U.S. Appl. No. 14/602,392 dated Mar. 1, 2018.
Sano, A., et al., Adaptive control of arterial oxygen pressure of newborn infants under incubator oxygen treatments, Journals and Magazines, IEEE Proceedings D—Control Theory and Applications, Sep. 1985, vol. 132, Issue 5, Abstract Only.
PCT, International Search Report and Written Opinion in International application No. PCT/US2020/057823 dated Jan. 28, 2021.
USPTO, Non-Final Office Action in U.S. Appl. No. 16/722,722 dated Dec. 22, 2020.
USPTO; Final Action for U.S. Appl. No. 16/672,638 dated Dec. 9, 2022, 21 pages.
USPTO; Non-Final Action for U.S. Appl. No. 16/672,638 dated Jul. 28, 2022, 15 pages.
USPTO, Non-Final Office Action for related U.S. Appl. No. 17/403,192, dated Oct. 6, 2022, 32 pages.

\* cited by examiner

METHODS, SYSTEMS, AND DEVICES FOR CONTROLLING MECHANICAL VENTILATION

TECHNICAL FIELD

The present disclosure generally relates to mechanical ventilators. More specifically, the disclosure applies methods, systems, and devices for controlling gas mixtures within mechanical ventilators.

BACKGROUND

A mechanical ventilator is a medical device that replaces or assists a patient with their spontaneous breathing. This medical device may also be called a respirator and/or a breathing machine. Patients requiring mechanical ventilation may be suffering from a form of acute lung injury (ALI) and in more severe cases may include acute respiratory distress syndrome (ARDS). ALI and ARDS result in hypoxemia, where a patient has abnormally low levels of oxygen in the blood. As examples, pneumonia and sepsis may require a patient to be mechanically ventilated. If mechanical ventilation is not properly applied, lung injury may result. This is sometimes referred to as ventilator-induced lung injury (VILI). An important function of a mechanical ventilator is controlling fraction of inspired oxygen in air ($FiO_2$) mixture that the patient receives. This function is normally provided by a gas blender. If not properly regulated, patients may suffer worsening hypoxemia. If the oxygen level is regulated too high the patient may experience hyperoxia, where organs, tissues, and cells are exposed to an excess supply of oxygen.

Accordingly, a need exists for improved methods, systems, and devices for controlling gas mixtures in mechanical ventilators.

SUMMARY

Disclosed herein are methods, systems, and devices for controlling a gas mixture within a mechanical ventilator. According to one embodiment, a computer implemented method includes receiving first peripheral arterial oxygen saturation ($SpO_2$) data from a pulse oximeter via a pulse oximeter interface. In this embodiment the pulse oximeter is configured to monitor a patient receiving invasive ventilation and a ventilator mechanism is configured to provide at least a portion of the invasive ventilation.

The computer implemented method also includes determining a first mode of operation for the ventilator mechanism. The computer implemented method further includes determining first partial pressure of oxygen ($PaO_2$) data stored in a first lookup table using the first $SpO_2$ data. The first lookup table is derived from a sigmoid shaped oxyhemoglobin dissociation curve. The computer implemented method further includes determining first fraction of inspired oxygen in air ($FiO_2$) data for setting a mixture in a gas blender in the ventilator mechanism based on the first $PaO_2$ data and a variable offset and providing the $FiO_2$ data to the ventilator mechanism. In certain embodiments, determining the first $PaO_2$ data using the first $SpO_2$ data further comprising converting a first $SpO_2$ value from the first $SpO_2$ data to a first $PaO_2$ value using interpolation upon determining the first $SpO_2$ value is not present in the first lookup table.

In some embodiments, the first mode of operation may be an initialization mode of operation for the ventilator mechanism. Determining the first $FiO_2$ data may be based on the first $PaO_2$ data having a relationship that is approximately linear with the first $FiO_2$ data plus the variable offset. This relationship may be defined approximately as $PaO_2=KLi(FiO_2)+K2$. KLi may be an initial lung function gain and K2 may be the variable offset. KLi may be a fixed value during the initialization mode of operation for the ventilator mechanism. KLi may also be determined from an entry by a healthcare professional via a user interface. The user interface may be configured to receive setup information and present status information to the healthcare professional regarding the patient and ventilator mechanism. The entry by the healthcare professional may be an initial $FiO_2$ value.

In some embodiments, the computer implemented method may further comprise determining the variable offset stored in a second lookup table using the first $PaO_2$ data. The second lookup table may map a plurality of variable offsets to a plurality of respiratory distress levels. Each respiratory distress level of the plurality of respiratory distress levels may be further mapped to a separate $PaO_2$ data range. A first respiratory distress level of the plurality of respiratory distress levels may be mapped to a first $PaO_2$ data range that includes values ranging between 80 millimeters of Mercury (mmHg) to 120 mmHg, and the first respiratory distress level may be mapped to a first variable offset of the plurality of variable offsets having a value between +15 mmHg and +25 mmHg A second respiratory distress level of the plurality of respiratory distress levels may be mapped to a second $PaO_2$ data range that includes values ranging between 63 mmHg to 65 mmHg, and the second respiratory distress level may be mapped to a second variable offset of the plurality of variable offsets having a value between +5 mmHg and +15 mmHg A third respiratory distress level of the plurality of respiratory distress levels may be mapped to a third $PaO_2$ data range that includes values ranging between 53 mmHg to 56 mmHg, and the third respiratory distress level may be mapped to a third variable offset of the plurality of variable offsets having a value between −5 mmHg and +5 mmHg.

In some embodiments, the computer implemented method may further include (1) determining a second mode of operation for the ventilator mechanism, (2) receiving second $SpO_2$ data from the pulse oximeter via the pulse oximeter interface, (3) determining second $PaO_2$ data stored in the first lookup table using the second $SpO_2$ data, (4) determining second $FiO_2$ data for setting the mixture based on the second $PaO_2$ data, and (5) providing the second $FiO_2$ data to the ventilator mechanism. In certain embodiments, the second mode of operation may be a steady-state mode of operation for the ventilator mechanism.

In some embodiments, determining the second $FiO_2$ data may also be based on the second $PaO_2$ data having a relationship that is approximately linear with the second $FiO_2$ data. The relationship may be defined approximately as $PaO_2=KL(FiO_2)$, wherein an offset such as the variable offset of the first mode of operation is not used. KL may be a variable lung function gain. KL may be updated on an ongoing interval between eight and twelve seconds. In other embodiments the ongoing interval may be less than eight seconds. In still other embodiments, the ongoing interval may be greater than twelve seconds.

In another embodiment, a computing device includes a memory and at least one processor configured to provide a method for controlling a gas mixture within a mechanical ventilator. The method includes receiving first $SpO_2$ data from a pulse oximeter via a pulse oximeter interface. In this embodiment the pulse oximeter is also configured to monitor a patient receiving invasive ventilation and a ventilator mechanism is configured to provide at least a portion of the invasive ventilation.

The method also includes determining a first mode of operation for the ventilator mechanism. The method further includes determining first $PaO_2$ data stored in a first lookup table using the first $SpO_2$ data. The first lookup table is derived from a sigmoid shaped oxyhemoglobin dissociation curve. The method further includes determining first $FiO_2$ data for setting a mixture in a gas blender in the ventilator mechanism based on the first $PaO_2$ data and a variable offset, and providing the $FiO_2$ data to the ventilator mechanism.

In another embodiment, a non-transitory computer-readable storage medium is disclosed. The non-transitory computer-readable storage medium stores computer instructions to be implemented on at least one computing device including at least one processor. The computer instructions when executed by the at least one processor cause the at least one computing device to perform a method for controlling a gas mixture within a mechanical ventilator. The method includes receiving first $SpO_2$ data from a pulse oximeter via a pulse oximeter interface. In this embodiment the pulse oximeter is also configured to monitor a patient receiving invasive ventilation and a ventilator mechanism is configured to provide at least a portion of the invasive ventilation.

The method also includes determining a first mode of operation for the ventilator mechanism. The method further includes determining first $PaO_2$ data stored in a first lookup table using the first $SpO_2$ data. The first lookup table is derived from a sigmoid shaped oxyhemoglobin dissociation curve. The method further includes determining first $FiO_2$ data for setting a mixture in a gas blender in the ventilator mechanism based on the first $PaO_2$ data and a variable offset and providing the $FiO_2$ data to the ventilator mechanism.

The features and advantages described in this summary and the following detailed description are not all-inclusive. Many additional features and advantages will be apparent to one of ordinary skill in the art in view of the drawings, specification, and claims presented herein.

BRIEF DESCRIPTION OF THE DRAWINGS

The present embodiments are illustrated by way of example and are not intended to be limited by the figures of the accompanying drawings. In the drawings.

DETAILED DESCRIPTION

Figure 1:
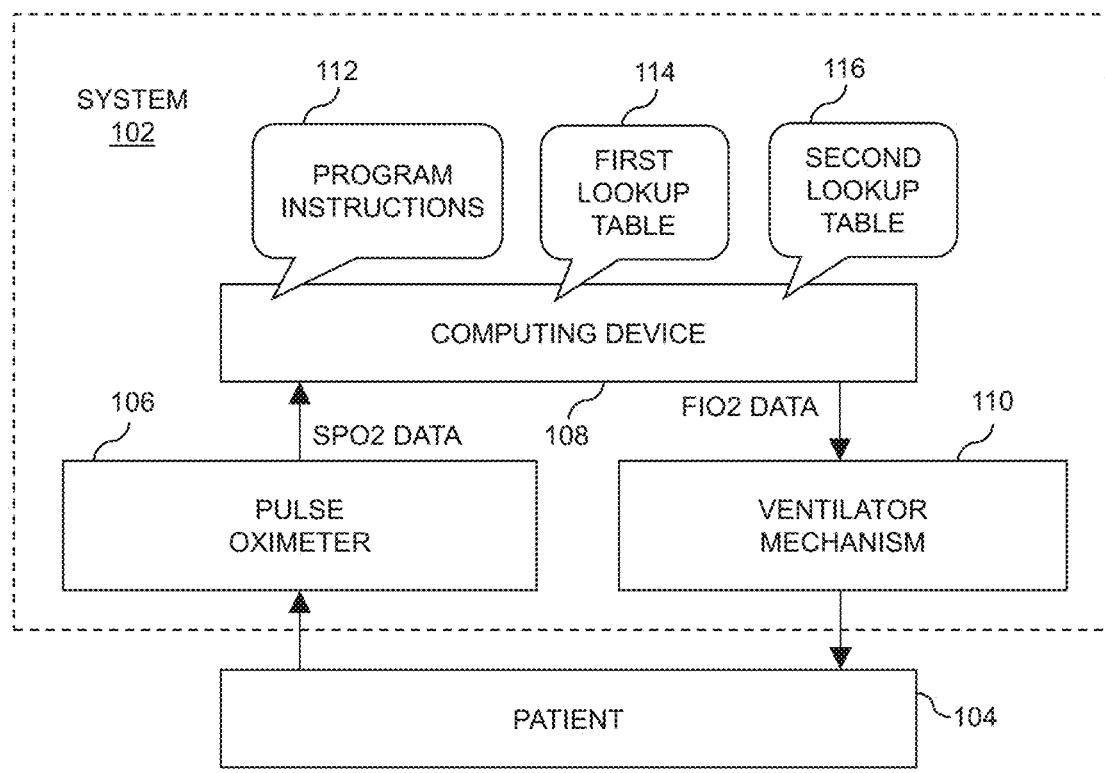
FIG. 1 depicts a block diagram illustrating a system for providing invasive ventilation for a patient in accordance with embodiments of the present disclosure.

Disclosed herein are methods, systems, and devices for controlling gas mixtures within mechanical ventilators.

The following description and figures are illustrative and are not to be construed as limiting. Numerous specific details are described to provide a thorough understanding of the disclosure. However, in certain instances, well-known or conventional details are not described in order to avoid obscuring the description. References to "one embodiment" or "an embodiment" in the present disclosure can be, but not necessarily are, references to the same embodiment and such references mean at least one of the embodiments.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way.

Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and is not intended to further limit the scope and meaning of the disclosure or of any exemplified term. Likewise, the disclosure is not limited to various embodiments given in this specification.

Without intent to limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

FIG. 1 depicts a block diagram 100 illustrating a system 102 for providing invasive ventilation for a patient 104 in accordance with embodiments of the present disclosure. The system 100 includes a pulse oximeter 106, a computing device 108, and a ventilator mechanism 110. The pulse oximeter 106 is configured to provide peripheral arterial oxygen saturation ($SpO_2$) data to the computing device 108. The $SpO_2$ data indicates an estimation of blood oxygen concentration and may be given as a percentage or ratio. Other terms for blood oxygen concentration may include peripheral oxygen saturation, blood oxygen saturation, and blood oxygen. The pulse oximeter 106 may be configured to be placed on a fingertip or an earlobe of the patient 104. The pulse oximeter 106 may be configured with two light emitting diodes (LEDs) operating at two different wavelengths (e.g. 660 nanometers and 940 nanometers) to determine a difference in absorption through the fingertip or earlobe. The difference in absorption provides a ratio of oxygenated hemoglobin to deoxygenated hemoglobin thus providing an indication of blood oxygen concentration.

The computing device 108 includes program instructions 112 and when executed determine partial pressure of oxygen ($PaO_2$) data using the $SpO_2$ data and a first lookup table 114. The first lookup table 114 is derived from a sigmoid shaped oxyhemoglobin dissociation curve. An example for the first lookup table 114 is shown in Table 1. Interpolation may be used to determine a $PaO_2$ value when the exact $SpO_2$ is not in the first lookup table 114. In certain embodiments, the first lookup table 114 may be included with the program instructions 112.

TABLE 1

| $SpO_2$ (%) | $PaO_2$ (mmHg) |
|---|---|
| 10 | 10 |
| 30 | 19 |
| 40 | 23 |
| 50 | 26.5 |
| 60 | 32 |
| 70 | 37 |
| 80 | 44.4 |
| 81 | 45 |
| 82 | 46 |
| 83 | 47 |
| 84 | 49 |
| 85 | 50 |
| 86 | 52 |
| 87 | 53 |
| 88 | 55 |
| 89 | 57 |
| 90 | 60 |
| 91 | 62 |
| 92 | 65 |
| 93 | 69 |
| 94 | 73 |
| 95 | 79 |
| 96 | 86 |
| 97 | 96 |
| 97.5 | 100 |
| 98 | 112 |
| 99 | 145 |
| 99.75 | 150 |

The computing device 108 is further configured to determine fraction of inspired oxygen in air ($FiO_2$) data using the $PaO_2$ data. $FiO_2$ data may be given as a percentage or ratio. Depending on a mode of operation, the computing device 108 may also use a second lookup table 116 to determine the $FiO_2$ data using a variable offset.

When in an initialization mode of operation (i.e. a first mode of operation), $FiO_2$ data is determined based on the $PaO_2$ data having a relationship that is approximately linear with the first $FiO_2$ data plus the variable offset. The relationship is defined approximately as $PaO_2=KLi(FiO_2)+K2$. KLi is an initial lung function gain and K2 is the variable offset.

KLi remains a fixed value during the initialization mode of operation and is determined from an initial $FiO_2$ value using the equation $KLi=PaO_2/FiO_2$. The initial $FiO_2$ is derived from an entry by a healthcare professional via a user interface (UI) or graphical user interface (GUI) associated with the computing device 108. The UI or GUI may be embedded with the computing device 108 or may be wired or wirelessly detached. The UI or GUI may be configured to receive additional setup information and present status/monitoring information to the healthcare professional regarding the patient 104 and ventilator mechanism.

The variable offset (K2) is cited in Sano, et al., "*Adaptive control of arterial oxygen pressure of newborn infants under incubator oxygen treatments*", IEE Proceedings D—Control Theory and Applications (Volume: 132, Issue: 5, September 1985) pages 205-211 which is hereby incorporated by reference in its entirety. The variable offset may have a range of zero to twenty. The value is near zero when the patient 104 is suffering from severe respiratory distress and the value is near twenty when the patient 104 is suffering from mild respiratory distress. Using the relationship of $PaO_2=KLi(FiO_2)+K2$, the system 102 may effectively treat patients in general regardless of scope of respiratory distress.

Disclosed herein is a method that uses the second lookup table 116 to identify variable offset (K2) values associated with ranges of $PaO_2$ The ranges of $PaO_2$ of and values of the variable offset identify with a "zone of distress" (i.e. "distress level") and are shown in Table 2. In certain embodiments, the second lookup table 116 may be included with the program instructions 112.

TABLE 2

| $PaO_2$ (mmHg) | Variable Offset (mmHg) | Distress Level |
|---|---|---|
| 69-150 | 20 | First |
| 60-68 | 10 | Second |
| 50-59 | 0 | Third |

Once the system enters a steady-state mode of operation (i.e. a second mode of operation) the variable offset is no longer needed and the relationship between $PaO_2=KL(FiO_2)$ may be defined as just $PaO_2=KL(FiO_2)$ without using K2. In this equation, KL is a variable lung gain function that is updated on an ongoing interval. The ongoing interval is typically between eight and twelve seconds. The equation $KL=PaO_2/FiO_2$ is used to calculate the update for KL.

In some embodiments, TABLE 1 and TABLE 2 may be implemented as a single table as shown in TABLE 3. Basically the first and second lookup tables are a single/combined lookup table. In certain embodiments, the single/combined lookup table 116 may be included with the program instructions 112.

TABLE 3

| $SpO_2$ (%) | $PaO_2$ (mmHg) | Offset (mmHg) | Distress Level |
|---|---|---|---|
| 10 | 10 | n/a | n/a |
| 30 | 19 | n/a | n/a |
| 40 | 23 | n/a | n/a |
| 50 | 26.5 | n/a | n/a |
| 60 | 32 | n/a | n/a |
| 70 | 37 | n/a | n/a |
| 80 | 44.4 | n/a | n/a |
| 81 | 45 | n/a | n/a |
| 82 | 46 | n/a | n/a |
| 83 | 47 | n/a | n/a |
| 84 | 49 | n/a | n/a |
| 85 | 50 | 0 | Third |
| 86 | 52 | 0 | Third |
| 87 | 53 | 0 | Third |
| 88 | 55 | 0 | Third |
| 89 | 57 | 0 | Third |
| 90 | 60 | 10 | Second |

TABLE 3-continued

| SpO$_2$ (%) | PaO$_2$ (mmHg) | Offset (mmHg) | Distress Level |
|---|---|---|---|
| 91 | 62 | 10 | Second |
| 92 | 65 | 10 | Second |
| 93 | 69 | 20 | First |
| 94 | 73 | 20 | First |
| 95 | 79 | 20 | First |
| 96 | 86 | 20 | First |
| 97 | 96 | 20 | First |
| 97.5 | 100 | 20 | First |
| 98 | 112 | 20 | First |
| 99 | 145 | 20 | First |
| 99.75 | 150 | 20 | First |

Note:
Tables 1-3 are for illustrative purposes only and are not intended for the actual treatment of any patient.

The computing device 108 is further configured to provide the FiO$_2$ data to the ventilator mechanism 110. The ventilator mechanism 110 is configured to provide at least a portion of the invasive ventilation for the patient 104. The FiO$_2$ data received from the computing device is used to control a gas concentration. The gas concentration may be implemented as a gas blender (not shown in FIG. 1) within the ventilator mechanism 110. In certain embodiments, the gas blender is provided by a mixing chamber fed with two solenoid-controlled valves. A first valve controls the flow of oxygen and a second valve controls the flow of air. By independently controlling the first valve and the second valve the volumetric fraction of oxygen provided by the ventilator mechanism 110 may be adjusted based on the FiO$_2$ data.

Figure 2:
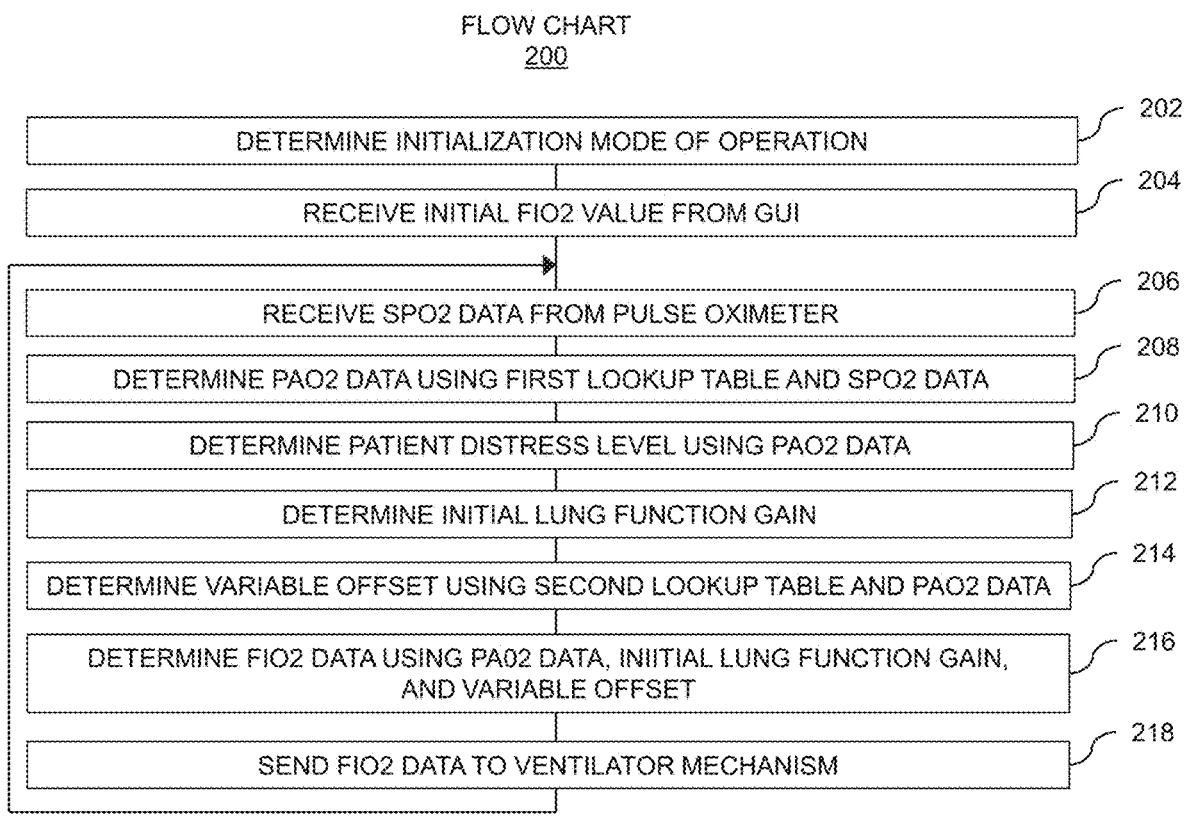
FIG. 2 depicts a flowchart illustrating a method for controlling a gas mixture within a mechanical ventilator in an initialization mode in accordance with embodiments of the present disclosure.

FIG. 2 depicts a flowchart 200 illustrating a method for controlling the gas mixture within the ventilator mechanism 110 of FIG. 1 while in an initialization mode (i.e. startup) in accordance with embodiments of the present disclosure.

In step 202, the computing device 108 determines that the system 102 is in an initialization mode of operation. This may be provided from the UI or GUI. The UI or GUI may be embedded with the computing device 108 or may be wired or wirelessly detached. The initialization mode of operation may be entered by a healthcare provider using the UI or GUI.

In step 204, the computing device 108 receives an initial FiO$_2$ value entered by the healthcare provider from the UI or GUI.

In step 206, the computing device 108 receives SpO$_2$ data from the pulse oximeter 106.

In step 208, the computing device 108 determines PaO$_2$ data using the first lookup table 114 and the SpO$_2$ data.

Optionally, in step 210, the computing device 108 determines a patient distress level based on the PaO$_2$ data.

In step 212, the computing device 108 determines an initial lung function gain (KLi) using the initial FiO$_2$ value and the equation KLi=PaO$_2$/FiO$_2$.

In step 214, the computing device 108 determines the variable offset (K2) using the second lookup table 116 and the PaO$_2$ data.

In step 216, the computing device 108 determines the FiO$_2$ data using the equation PaO$_2$=KLi(FiO$_2$)+K2.

In step 218, the computing device 108 sends the FiO$_2$ data to the ventilator mechanism 110. The computing device 108 continues to repeat steps 206 through 218 with the exception of step 212 while in the initialization mode of operation.

Figure 3:
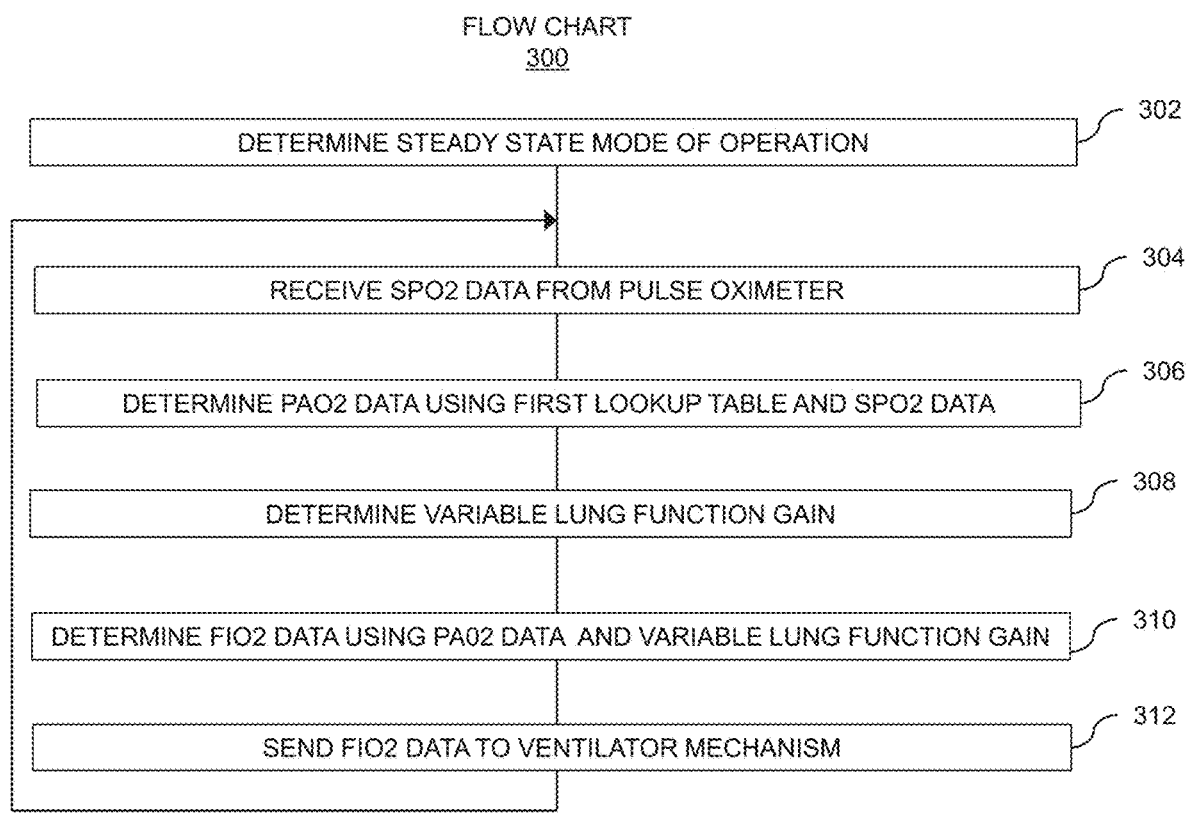
FIG. 3 depicts a flowchart illustrating a method for controlling a gas mixture within the mechanical ventilator in a steady-state mode in accordance with embodiments of the present disclosure.

FIG. 3 depicts a flowchart 300 illustrating a method for controlling the gas mixture within the ventilator mechanism 110 of FIG. 1 while in a steady-state mode (i.e. adaptive mode) in accordance with embodiments of the present disclosure.

In step 302, the computing device 108 determines that the system 102 is in a steady-state mode of operation In step 304, the computing device 108 receives SpO$_2$ data from the pulse oximeter 106.

In step 306, the computing device 108 determines the PaO$_2$ data using the first lookup table 114 and the SpO$_2$ data.

In step 308, the computing device 108 determines the variable lung function gain (KL) using the equation KL=PaO$_2$/FiO$_2$. In certain embodiments, KL is recalculated and updated on an ongoing interval between eight and twelve seconds. In other embodiments, KL is recalculated and updated on an ongoing interval that is less than eight seconds. In still other embodiments, KL is recalculated and updated on an ongoing interval that is greater than twelve seconds.

In step 310, the computing device 108 determines the FiO$_2$ data without the variable offset (K2) using the equation PaO$_2$=KLi(FiO$_2$).

In step 312, the computing device 108 sends the FiO$_2$ data to the ventilator mechanism 110. The computing device 108 continues to repeat steps 304 through 312 while in the steady-state mode of operation.

Figure 4:
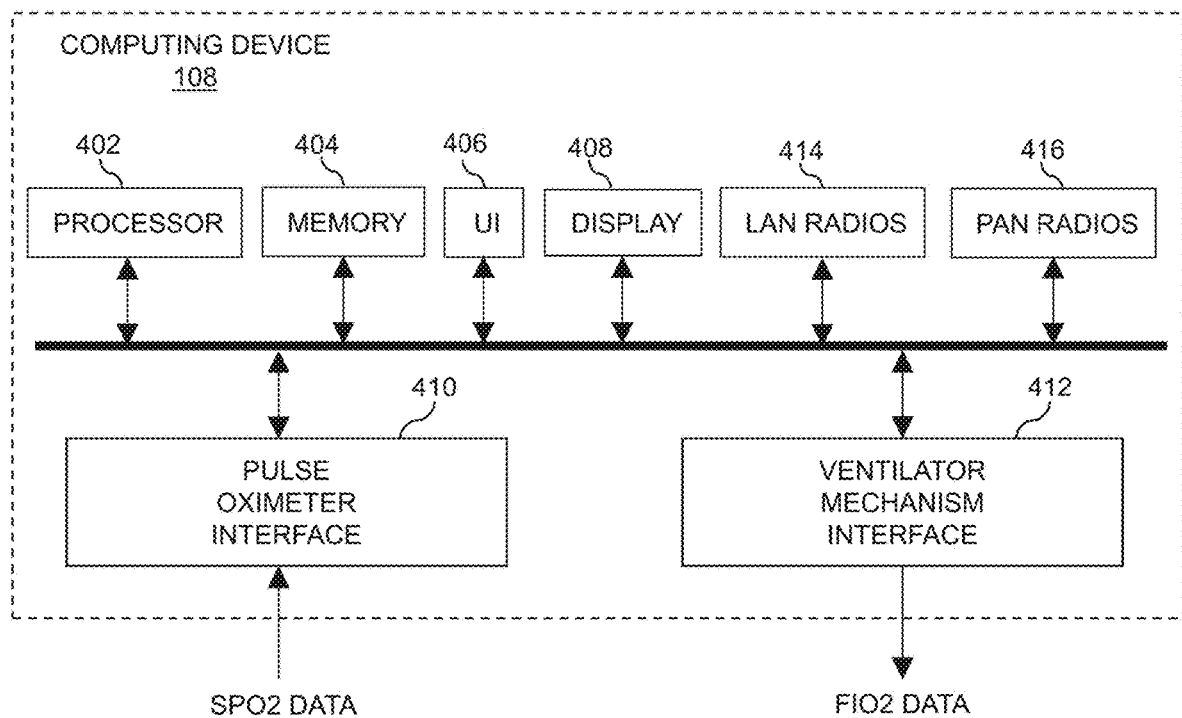
FIG. 4 depicts a block diagram illustrating a computing device for controlling a gas mixture within the mechanical ventilator in accordance with embodiments of the present disclosure.

FIG. 4 depicts a block diagram illustrating the computing device 108 of FIG. 1 in accordance with embodiments of the present disclosure. The computing device 108 includes a processor 402 and memory 404. The memory 404 may include a combination of volatile memory (e.g. random access memory) and non-volatile memory (e.g. flash memory). The memory 404 may be partially integrated with the processor 402. In certain embodiments, the processor 402 and the memory 404 may be implemented using a microcontroller. For example, the microcontroller may be the Freescale® medical-oriented, microcontroller Kinetis K53. In other embodiments, processor 402 may be a proportional-integral-derivative (PID) controller.

The computing device 108 also includes a UI 406 and a display 408. The UI 406 and display 408 may be integrated such as a touchpad display and also may be a GUI. The computing device 108 includes a pulse oximeter interface 410 for receiving SpO$_2$ data from the pulse oximeter 106. The pulse oximeter interface 410 may be wired electrical interface including analog and/or digital signals. In other embodiments, the pulse oximeter interface 410 may be a wireless interface or an optical interface.

The computing further includes a ventilator mechanism interface 412 for providing FiO$_2$ data to the ventilator mechanism 110. The ventilator mechanism interface 412 may be a wired electrical interface including analog and/or digital signals. In other embodiments, the ventilator mechanism interface 412 may be a wireless interface or an optical interface.

In certain embodiments, the computing device 108 may also include one or more local area network (LAN) radios 414 and one or more personal area network (PAN) radios 416. The LAN radios 414 may include Wi-Fi technologies such as 802.11a, 802.11b/g/n, and/or 802.11ac circuitry. The PAN radios 416 may include one or more Bluetooth® technologies. The LAN radios 414 and/or the PAN radios 416 may also provide connectivity to one or more remote GUIs located at a nurses station or another healthcare monitoring location.

In some embodiments, the computing device 108 may be a dedicated medical-grade computer having UL60601-1, EN60601-1, and/or IEC60601-1 certifications.

In conclusion; this disclosure provides methods, systems, and devices for controlling gas mixtures within mechanical ventilators. The disclosed initialization mode of operation uses a variable offset (K2) which allows the a system to start an adaptive process in a steady-state condition such that matching of oxygen to the needs of patients is optimal independent of patients' level of distress. The disclosed initialization mode of operation also uses an initial lung gain function (KLi) that is determined based on an entry of a healthcare provider.

As will be appreciated by one skilled in the art, aspects of the present disclosure may be embodied as a system, method or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium (including, but not limited to, non-transitory computer readable storage media). A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including object oriented and/or procedural programming languages. Programming languages may include, but are not limited to: Ruby, JavaScript, Java, Python, Ruby, PHP, C, C++, C#, Objective-C, Go, Scala, Swift, Kotlin, OCaml, SAS, Tensorflow, CUDA, or the like. The program code may execute entirely on the user's computer, partly on the user's computer, as a stand-alone software package, partly on the user's computer, and partly on a remote computer or entirely on the remote computer or server. In the latter situation scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described herein with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions.

These computer program instructions may be provided to a processor of a general purpose computer, special purpose computer, or other programmable data processing apparatus to produce a machine, such that the instructions, which execute via the processor of the computer or other programmable data processing apparatus, create an ability for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The disclosure has been presented for purposes of illustration and description, but is not intended to be exhaustive or limited in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer implemented method comprising:
   receiving first peripheral arterial oxygen saturation ($SpO_2$) data from a pulse oximeter via a pulse oximeter interface, wherein the pulse oximeter is configured to monitor a patient receiving invasive ventilation;
   determining a first mode of operation for a ventilator mechanism, wherein the ventilator mechanism is configured to provide at least a portion of the invasive ventilation;
   determining first partial pressure of oxygen ($PaO_2$) data stored in a first lookup table using the first $SpO_2$ data, wherein the first lookup table is derived from a sigmoid shaped oxyhemoglobin dissociation curve;
   determining a variable offset stored in a second lookup table using the first $PaO_2$ data;
   determining first fraction of inspired oxygen in air ($FiO_2$) data for setting a mixture in a gas blender in the ventilator mechanism based on the first $PaO_2$ data and the variable offset;
   and
   providing the $FiO_2$ data to the ventilator mechanism, wherein:
   the first mode of operation is an initialization mode of operation for the ventilator mechanism;
   determining the first $FiO_2$ data is based on the first $PaO_2$ data having a relationship that is approximately linear with the first $FiO_2$ data plus the variable offset; and
   the second lookup table maps a plurality of variable offsets to a plurality of respiratory distress levels.

2. The computer implemented method of claim 1, wherein the relationship is defined approximately as $PaO_2 = KLi(FiO_2) + K2$, wherein KLi is an initial lung function gain and K2 is the variable offset.

3. The computer implemented method of claim 2, wherein:
   KLi is a fixed value during the initialization mode of operation for the ventilator mechanism;
   KLi is determined from an entry by a healthcare professional via a user interface; and
   the user interface is configured to receive setup information and present status information to the healthcare professional regarding the patient and ventilator mechanism.

4. The computer implemented method of claim 3, wherein the entry by the healthcare professional is an initial $FiO_2$ value.

5. The computer implemented method of claim 1, wherein each respiratory distress level of the plurality of respiratory distress levels is further mapped to a separate $PaO_2$ data range.

6. The computer implemented method of claim 5, wherein:
   a first respiratory distress level of the plurality of respiratory distress levels is mapped to a first $PaO_2$ data range that includes values ranging between 80 millimeters of Mercury (mmHg) to 120 mmHg; and
   the first respiratory distress level is mapped to a first variable offset of the plurality of variable offsets having a value between +15 mmHg and +25 mmHg.

7. The computer implemented method of claim 6, wherein:
   a second respiratory distress level of the plurality of respiratory distress levels is mapped to a second $PaO_2$ data range that includes values ranging between 63 mmHg to 65 mmHg; and
   the second respiratory distress level is mapped to a second variable offset of the plurality of variable offsets having a value between +5 mmHg and +15 mmHg.

8. The computer implemented method of claim 7, wherein:
   a third respiratory distress level of the plurality of respiratory distress levels is mapped to a third $PaO_2$ data range that includes values ranging between 53 mmHg to 56 mmHg; and
   the third respiratory distress level is mapped to a third variable offset of the plurality of variable offsets having a value between −5 mmHg and +5 mmHg.

9. The computer implemented method of claim 1, wherein determining the first $PaO_2$ data using the first $SpO_2$ data further comprising converting a first $SpO_2$ value from the first $SpO_2$ data to a first $PaO_2$ value using interpolation upon determining the first $SpO_2$ value is not present in the first lookup table.

10. The computer implemented method of claim 1 further comprising:
    determining a second mode of operation for the ventilator mechanism;
    receiving second $SpO_2$ data from the pulse oximeter via the pulse oximeter interface;
    determining second $PaO_2$ data stored in the first lookup table using the second $SpO_2$ data;
    determining second $FiO_2$ data for setting the mixture based on the second $PaO_2$ data; and
    providing the second $FiO_2$ data to the ventilator mechanism.

11. The computer implemented method of claim 10, wherein the second mode of operation is a steady-state mode of operation for the ventilator mechanism.

12. The computer implemented method of claim 11, wherein determining the second $FiO_2$ data is based on the second $PaO_2$ data having a relationship that is approximately linear with the second $FiO_2$ data.

13. The computer implemented method of claim 12, wherein the relationship is defined approximately as $PaO_2=KL(FiO_2)$, wherein KL is a variable lung function gain.

14. The computer implemented method of claim 10, wherein KL is updated on an ongoing interval between eight and twelve seconds.

15. The computer implemented method of claim 10, wherein determining the second $PaO_2$ data using the second $SpO_2$ data further comprising converting a second $SpO_2$ value from the second $SpO_2$ data to second first $PaO_2$ value using interpolation upon determining the second $SpO_2$ value is not present in the first lookup table.

16. A computing device comprising:
a memory; and
at least one processor configured for:
receiving first peripheral arterial oxygen saturation ($SpO_2$) data from a pulse oximeter via a pulse oximeter interface, wherein the pulse oximeter is configured to monitor a patient receiving invasive ventilation;
determining a first mode of operation for a ventilator mechanism, wherein the ventilator mechanism is configured to provide at least a portion of the invasive ventilation;
determining first partial pressure of oxygen ($PaO_2$) data stored in a first lookup table using the first $SpO_2$ data, wherein the first lookup table is derived from a sigmoid shaped oxyhemoglobin dissociation curve;
determining a variable offset stored in a second lookup table using the first $PaO_2$ data;
determining first fraction of inspired oxygen in air ($FiO_2$) data for setting a mixture in a gas blender in the ventilator mechanism based on the first $PaO_2$ data and the variable offset; and
providing the $FiO_2$ data to the ventilator mechanism, wherein:
the first mode of operation is an initialization mode of operation for the ventilator mechanism;
determining the first $FiO_2$ data is based on the first $PaO_2$ data having a relationship that is approximately linear with the first $FiO_2$ data plus the variable offset; and
the second lookup table maps a plurality of variable offsets to a plurality of respiratory distress levels.

17. A non-transitory computer-readable storage medium, storing one or more programs for execution by one or more processors of a computing device, the one or more programs including instructions for:
receiving first peripheral arterial oxygen saturation ($SpO_2$) data from a pulse oximeter via a pulse oximeter interface, wherein the pulse oximeter is configured to monitor a patient receiving invasive ventilation;
determining a first mode of operation for a ventilator mechanism, wherein the ventilator mechanism is configured to provide at least a portion of the invasive ventilation;
determining first partial pressure of oxygen ($PaO_2$) data stored in a first lookup table using the first $SpO_2$ data, wherein the first lookup table is derived from a sigmoid shaped oxyhemoglobin dissociation curve;
determining a variable offset stored in a second lookup table using the first $PaO_2$ data;
determining first fraction of inspired oxygen in air ($FiO_2$) data for setting a mixture in a gas blender in the ventilator mechanism based on the first $PaO_2$ data and the variable offset; and
providing the $FiO_2$ data to the ventilator mechanism, wherein:
the first mode of operation is an initialization mode of operation for the ventilator mechanism;
determining the first $FiO_2$ data is based on the first $PaO_2$ data having a relationship that is approximately linear with the first $FiO_2$ data plus the variable offset; and
the second lookup table maps a plurality of variable offsets to a plurality of respiratory distress levels.

* * * * *